(12) United States Patent
Lipovsek

(10) Patent No.: US 10,150,962 B2
(45) Date of Patent: Dec. 11, 2018

(54) METHODS FOR THE SELECTION OF BINDING PROTEINS

(71) Applicant: BRISTOL-MYERS SQUIBB COMPANY, Princeton, NJ (US)

(72) Inventor: Dasa Lipovsek, Cambridge, MA (US)

(73) Assignee: Bristol-Myers Squibb Company, Princeton, NJ (US)

(*) Notice: Subject to any disclaimer, the term of this patent is extended or adjusted under 35 U.S.C. 154(b) by 114 days.

(21) Appl. No.: 15/142,651

(22) Filed: Apr. 29, 2016

(65) Prior Publication Data
US 2016/0237423 A1 Aug. 18, 2016

Related U.S. Application Data

(62) Division of application No. 14/117,689, filed as application No. PCT/US2012/038032 on May 16, 2012, now Pat. No. 9,347,058.

(60) Provisional application No. 61/487,032, filed on May 17, 2011.

(51) Int. Cl.
| | | |
|---|---|---|
| C40B 30/04 | (2006.01) | |
| C12N 15/10 | (2006.01) | |
| G01N 33/68 | (2006.01) | |

(52) U.S. Cl.
CPC ..... *C12N 15/1037* (2013.01); *G01N 33/6845* (2013.01); *C40B 30/04* (2013.01)

(58) Field of Classification Search
None
See application file for complete search history.

(56) References Cited

U.S. PATENT DOCUMENTS

| | | |
|---|---|---|
| 6,114,147 A | 9/2000 | Frenken et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,518,018 B1 | 2/2003 | Szostak et al. |
| 6,673,901 B2 | 1/2004 | Koide |
| 6,818,418 B1 | 11/2004 | Lipovsek et al. |
| 7,115,396 B2 | 10/2006 | Lipovsek et al. |
| 2003/0186385 A1 | 10/2003 | Koide |

FOREIGN PATENT DOCUMENTS

| | | |
|---|---|---|
| WO | WO98/56915 | 12/1998 |
| WO | WO99/36569 | 7/1999 |
| WO | WO00/34784 | 6/2000 |
| WO | WO01/64942 A1 | 9/2001 |
| WO | WO02/32925 A2 | 4/2002 |
| WO | WO02/081497 A2 | 10/2002 |

(Continued)

OTHER PUBLICATIONS

Bowley et al., Libraries against libraries for combinatorial selection of replicating antigen-antibody pairs, PNAS, Feb. 3, 2009, pp. 1380-1385, vol. 106, No. 5.

(Continued)

*Primary Examiner* — Christian C Boesen
(74) *Attorney, Agent, or Firm* — Isabelle M. Clauss

(57) ABSTRACT

This application provides an improved screening method for the selection of target-binding proteins having desirable biophysical properties. The method combines mRNA display and yeast surface display in a way that takes advantage of the desirable attributes of both processes.

2 Claims, 6 Drawing Sheets

Specification includes a Sequence Listing.

(56) References Cited

FOREIGN PATENT DOCUMENTS

| WO | WO03/102020 A2 | 12/2003 |
|---|---|---|
| WO | WO2008/031098 A1 | 3/2008 |
| WO | WO2009/009045 A2 | 1/2009 |
| WO | WO2009/083804 A2 | 7/2009 |
| WO | WO2009/102421 A2 | 8/2009 |
| WO | WO2009/086116 A2 | 9/2009 |
| WO | WO2009/133208 A1 | 11/2009 |
| WO | WO2009/142773 A9 | 11/2009 |
| WO | WO2010/039850 A1 | 4/2010 |
| WO | WO2010/039852 A2 | 4/2010 |
| WO | WO2010/051274 A2 | 5/2010 |
| WO | WO2010/051310 A2 | 5/2010 |
| WO | WO2010/060095 A1 | 5/2010 |
| WO | WO2010/093627 A2 | 8/2010 |
| WO | WO2011/051333 A1 | 5/2011 |
| WO | WO2011/051466 A1 | 5/2011 |
| WO | WO2011/092233 A1 | 8/2011 |
| WO | WO2011/103105 A1 | 8/2011 |
| WO | WO2011/130324 A1 | 10/2011 |
| WO | WO2011/130328 A1 | 10/2011 |
| WO | WO2011/130354 A1 | 10/2011 |
| WO | WO2011/137319 A2 | 11/2011 |
| WO | WO2011/140086 A9 | 11/2011 |
| WO | WO2011/150133 A2 | 12/2011 |
| WO | WO2012/016245 A2 | 2/2012 |

OTHER PUBLICATIONS

Chen et al., Prokaryotic Coupled Transcription-Translation, Methods in Enzymology, 1983, pp. 674-690, vol. 101.
Ellman et al., Biosynthetic Method for Introducing Unnatural Amino Acids Site-Specifically into Proteins, Methods in Enzymology, 1991, pp. 301-336, vol. 202.
Gera et al., Protein selection using yeast surface display, Methods, 2013, pp. 15-26, vol. 60.
Gilbreth et al., A Dominant Conformational Role for Amino Acid Diversity in Minimalist Protein-Protein Interfaces, J. Mol. Biol., 2008, pp. 407-418, vol. 381.
Hackel et al., Stability and CDR Composition Biases Enrich Binder Functionality Landscapes, J. Mol. Biol., 2010, pp. 84-96, vol. 401.
Hu et al., Combinatorial libraries against libraries for selecting neoepitope activation-specific antibodies, PNAS, Apr. 6, 2010, pp. 6252-6257, vol. 107, No. 14.
Kiode et al., Target-Binding Proteins Based on the $10^{th}$ Human Fibronectin Type III Domain ($^{10}$FN3), Methods in Enzymology, 2012, pp. 135-156, vol. 503.
Kiode et al., High-affinity single-domain binding proteins with a binary-code interface, PNAS, Apr. 17, 2007, pp. 6632-6637, vol. 104, No. 16.
Leibowitz et al., In Vitro Protein Synthesis, Methods in Enzymology, 1991, pp. 536-545, vol. 194.
Lipovsek et al., Selection of Horseradish Peroxidase Variants with Enhanced Enantioslectivity by Yeast Surface Display, Chemistry & Biology, Oct. 2007, pp. 1176-1185, vol. 14.
Lipovsek et al., Evolution of an Interloop Disulfide Bond in High-Affinity Antibody Mimics Based on Fibronection Type III Doman and Selected by Yeast Surface Display: Molecular Convergence with Single-Domain Camelid and Sthark Antibodies, J. Mol. Biol., 2007, pp. 1024-1041, vol. 368.
Lipovsek, D., Adnectins: engineered target-binding protein therapeutics, Protein Engineering, Design & Selection, 2011, pp. 3-9. vol. 24, No. 1.
Rao, B., A "super-library" of alternate scaffolds for engineering molecular recognition, PEGS Meeting, May 18, 2010, North Carolina State University, pp. 1-23.
Roberts et al., RNA-peptide fusions for the in vitro selection of peptides and proteins, PNAS, Nov. 1997, pp. 12297-12302, vol. 94.
Wang et al., Adapter-Directed Display: A Modular Design for Shuttling Display on Phage Surfaces, J. Mol. Biol. 2010, pp. 1088-1101, vol. 395.
Xu et al., Directed Evolution of High-Affinity Antibody Mimics Using mRNA Display, Chemistry & Biology, Aug. 2002, pp. 933-942, vol. 9.
Zubay, G., In Vitro Synthesis of Protein in Microbial Systems, Annu. Rev. Genet, 1973, pp. 267-287.
Valencia et al., mRNA-Display-Based Selections for Proteins with Desired Functions: A Protease-Substrate Case Study, Biotechnol. Prog., 2008, pp. 561-569, vol. 24, No. 3.

METHODS FOR THE SELECTION OF BINDING PROTEINS

CROSS-REFERENCE TO RELATED APPLICATIONS

The present application is a divisional application of U.S. patent application Ser. No. 14/117,689, filed Nov. 14, 2013, which claims the benefit of International Application No. PCT/US2012/038032, filed May 16, 2012 which claims priority to U.S. provisional patent application No. 61/487,032, filed on May 17, 2011, the contents of which are specifically incorporated by reference herein.

BACKGROUND

The production of polypeptides with target protein-binding properties is of great economic interest. At present, a number of methods have been developed to screen large libraries and identify polypeptides with binding affinity to a protein of interest. Typically, a large number of genetically diverse polypeptide mutants are produced in a first step. In a second step these polypeptide mutants are selected according to their binding affinity to the protein of interest. This process for the production of diversity and subsequent targeted selection can be repeated as often as it is desired.

However, a protein that has high target binding affinity may not have sufficiently high stability and solubility. Even for those proteins that have high solubility, high concentration liquid formulations tend to have short shelf lives and may lose biological activity as a result of chemical and physical instabilities during the storage. For example, aggregate formation during storage of a liquid protein composition can adversely affect the biological activity of the protein, resulting in loss of therapeutic efficacy and/or an increase in immunogenicity in humans.

This application provides an improved screening method for the selection of target-binding proteins having desirable biophysical properties (e.g., high solubility, stability, etc.). The method combines mRNA display and yeast surface display in a way that takes advantage of the desirable attributes of both processes.

SUMMARY

Provided herein are methods for selecting at least one target-binding protein with favorable biophysical properties. A method may comprise (i) a first phase comprising selecting a first population of protein variants binding a target protein ("target-binding protein variants") from a library comprising at least about $10^{12}$ protein variants; and (ii) a second phase comprising selecting a second population of target-binding protein variants from at least a portion of the first population of target-binding protein variants using yeast surface display, wherein the second population of target-binding protein variants comprises at least one target-binding protein with favorable biophysical properties. The library may comprise at least about $10^{13}$ protein variants. The first phase may comprise at least one round of selection, wherein a round of selection comprises contacting the target protein with the library of protein variants, removing any protein variants that do not bind to the target with a desired affinity, and isolating the remaining protein variants. The first phase may comprise at least 2 consecutive rounds of selection. The first phase may comprise at least 3 to 4 consecutive rounds of selection. The first phase may comprise a number of rounds of selection sufficient to obtain at most $10^4$ to $10^8$ target-binding protein variants, e.g., $10^5$ to $10^7$ target-binding protein variants. The library of the first phase may be a library of mRNA-protein fusions. The mRNA-protein fusions may be covalently conjugated via a puromycin linker. The second phase may comprise at least one round of selection, wherein a round of selection comprises contacting the target protein with the first population of target-binding protein variants displayed on yeast cells, removing any yeast cells displaying protein variants that do not bind to the target with a desired affinity, to thereby select the second population of target-binding protein variants. The second phase may comprise at least 2 consecutive rounds of selection. The second phase may comprise at least 3 to 6 consecutive rounds of selection. The second phase may comprise a number of rounds of selection sufficient to obtain at most $10^3$ (or at most $10^2$) target-binding protein variants. The at least a portion of the first population of target-binding protein variants in the second phase may comprise at least $10^5$ target-binding protein variants. In an exemplary embodiment, the first phase comprises providing a library comprising at least $10^{12}$ protein variants and performing a number of rounds of selection of the library sufficient to obtain from $10^4$ to $10^8$ (e.g., $10^5$ to $10^7$) target-binding protein variants; and the second phase comprises performing a number of rounds of selection on at least a portion of the $10^4$ to $10^8$ (e.g., $10^5$ to $10^7$) target-binding protein variants of the first phase sufficient to obtain at most about $10^3$ target-binding protein variants. The second phase may comprise performing a number of rounds of selection sufficient to obtain at most about $10^2$ target-binding protein variants. The second phase may comprise at least one round of selection wherein at most the top 10% of the yeast cells that express the highest level of target-binding protein variants are selected. Each of the rounds of selection of yeast surface display may comprise selecting at most the top 10% of the yeast cells that express the highest level of target-binding protein variants. A method may further comprise affinity maturation during or after the first phase, during or after the second phase, or both. The favorable biophysical properties may be one or more of solubility, thermostability, high expression levels, low levels of aggregation, proper folding, or binding specificity. The method may increase the likelihood of selecting a target-binding protein variant that is monomeric by at least twofold relative to a method of selection that does not comprise a second phase using yeast display. The method may increase the likelihood of selecting a target-binding protein variant having a higher melting temperature relative to a method of selection that does not comprise a second phase using yeast display. In certain embodiments, the library of protein variants is a library of $^{10}$Fn3 variants. The $^{10}$Fn3 variants may comprise sequence modifications in the BC, DE or FG loops. The variants may comprise sequence modifications in at least one loop and at least one beta strand. One or more of the BC, DE and FG loops may be extended in length or reduced in length relative the length of the corresponding loop of the wild-type human $^{10}$Fn3 domain. In a particular example, the first phase comprises providing a library comprising at least $10^{12}$ protein variants and performing a number of rounds of selection of the library sufficient to obtain from $10^4$ to $10^8$ (e.g., $10^5$ to $10^7$) target-binding protein variants; and the second phase comprises performing a number of rounds of selection on at least a portion of the $10^4$ to $10^8$ (e.g., $10^5$ to $10^7$) target-binding protein variants sufficient to obtain at most about $10^3$ (e.g., at most $10^2$) target-binding protein variants, and wherein the library of protein variants is a library of $^{10}$Fn3 variants, wherein each protein variant comprises at least one modification in a loop and at least one modification in a beta strand relative to a wild-type $^{10}$Fn3 protein. The library of the first phase is a mRNA-display library.

Further provided herein are methods for selecting a target-binding protein with favorable biophysical properties comprising (i) providing from $10^4$ to $10^8$ (e.g., $10^5$ to $10^7$) target-binding protein variants selected from a library of protein variants comprising at least $10^{12}$ members; and (ii) selecting a population of at most $10^3$ (e.g., at most $10^2$) target-binding protein variants from at least $10^5$ target-binding protein variants of step (i) using yeast surface display. The $10^4$ to $10^8$ (e.g., $10^5$ to $10^7$) target-binding protein variants of step (i) may be selected from a library of protein variants comprising at least $10^{13}$ members.

Also encompassed herein are methods for selecting a target-binding protein with favorable biophysical properties comprising (i) selecting a first population of target-binding protein variants consisting of at most $10^3$ (e.g., at most $10^2$) target-binding protein variants from a library comprising at least about $10^{12}$ protein variants, comprising conducting a number of rounds of selection sufficient to obtain the at most $10^3$ (e.g., at most $10^2$) target-binding protein variants; (ii) determining whether a significant number of the at most $10^3$ (e.g., at most $10^2$) target-binding protein variants have favorable biophysical properties; and (iii) if a significant number of the at most $10^3$ (e.g., at most $10^2$) target-binding protein variants do not have favorable biophysical properties, then selecting a population of at most $10^3$ (e.g., at most $10^2$) target-binding protein variants from at least $10^5$ target-binding protein variants obtained during the selection in step (i) using yeast surface display. "Significant number" may refer to at least about 10%, 20%, 30%, 40%, 50%, 60%, 70%, 80% or 90%. Selecting a population of at least $10^3$ (e.g., at most $10^2$) target-binding protein variants from at least $10^5$ target-binding protein variants obtained during the selection in step (i) using yeast surface display may comprise selecting at most the top 10% of the yeast cells that express the highest level of target-binding protein variants. Each of the rounds of selection of yeast surface display may comprise selecting at most the top 10% of the yeast cells that express the highest level of target-binding protein variants.

The application provides a two-phase method for selecting one or more target-binding protein variants with favorable biophysical properties. Any type of protein may be screened according to the methods described herein, including, for example, scFvs, Fabs or $^{10}$Fn3 domain proteins. In an exemplary embodiment, the method involves screening a library of $^{10}$Fn3 domain protein variants. The library may comprise a plurality of $^{10}$Fn3 domain proteins having sequence modifications in one or more of the BC, DE and/or FG loops. In certain embodiments, one of more of the BC, DE and/or FG loops may be extended in length or reduced in length relative to the corresponding loop of the wild-type human $^{10}$Fn3 domain.

In certain embodiments, the first phase involves screening a library of RNA-protein fusions, wherein the mRNA-protein fusions are covalently conjugated via a puromycin linker.

In one aspect, the two-phase method comprises screening a library of protein variants against a target protein using mRNA display to select a population of target-binding protein variants. The second phase comprises screening the population of target-binding protein variants against the target protein using yeast surface display to select a sub-population of target-binding protein variants with favorable biophysical properties.

In certain embodiments, first phase comprises screening a library comprising at least $10^{12}$ protein variants using mRNA display.

In certain embodiments, the first phase of screening involves contacting the target protein with the library of protein variants, removing any protein variants that do not bind to the target with a desired affinity, and isolating the remaining protein variants.

In certain embodiments, the first phase of screening comprises the steps of a) producing a population of candidate RNA molecules that encode a plurality of candidate protein variant sequences, each RNA comprising a translation initiation sequence and a start codon operably linked to said candidate protein variant coding sequence and each being operably linked to a peptidyl acceptor at the 3' end; b) in vitro translating said candidate protein variant coding sequences to produce a population of candidate RNA-protein fusions; c) contacting said population of candidate RNA-protein fusions with a target protein; d) selecting a population of target-binding RNA-protein fusions, the protein portion of which has a binding affinity or specificity for the target protein; and e) recovering the genetic information encoding the population of target-binding protein variants by the reverse transcribing the RNA portion to produce complementary DNA.

In certain embodiments, the first phase of screening is repeated at least 2 consecutive times. In certain embodiments, the first phase of screening is repeated at least 3 to 4 consecutive times.

In certain embodiments, the second phase of screening involves contacting the target protein with the population of protein variants selected in the first phase, removing any protein variants that do not bind to the target with a desired affinity, and isolating the remaining protein variants.

In certain embodiments, the second phase of screening comprises the steps of a) displaying the population of protein variants on the surface of yeast cells, b) contacting the yeast cells with a target protein; and c) sorting the yeast cells based on the binding of the target protein thereby isolating the yeast cells expressing protein variants having the desired binding affinity for the target.

In certain embodiments, the second phase of screening is repeated at least 2 consecutive times. In certain embodiments, the second phase of screening is repeated at least 3 to 6 consecutive times.

In certain embodiments, the sub-population of target-binding protein variants with favorable biophysical properties comprises at least 100 protein variants.

In certain embodiments, the method further comprises affinity maturation following the first phase of screening, following the second phase of screening, or both. In certain embodiments, the method further comprises affinity maturation during the first phase of screening, during the second phase of screening, or both.

In certain embodiments, the favorable biophysical properties are one or more of solubility, thermostability, high expression levels, low levels of aggregation, proper folding and/or binding specificity.

In certain embodiments, the method increases the likelihood of selecting a target-binding protein variant that is monomeric by at least two-fold relative to a method involving screening the same library using only mRNA display.

In certain embodiments, the method increases the likelihood of selecting a target-binding protein variant having a higher melting temperature relative to a method involving screening the same library using only mRNA display.

DETAILED DESCRIPTION

Overview

Figure 1:
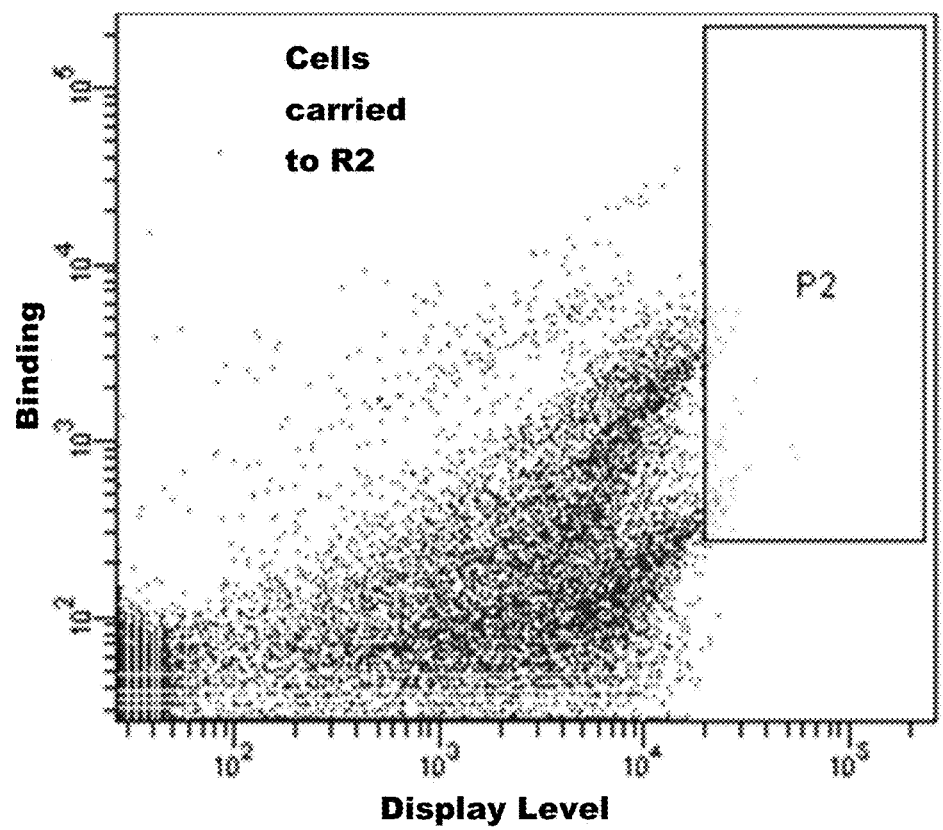
FIG. 1. Yeast population labeled in round 1 of yeast surface display. Relative "Display level" is revealed by fluorescent labeling of the C-terminal epitope tag, and "Binding" is quantified by labeling with fluorescently labeled PCSK9. The gate labeled "P2" contains yeast cells that are decorated with $^{10}$Fn3 domain proteins that both display at a high level and bind PCSK9; the cells in this gate were captured by fluorescence-activated cell sorting and used as the starting point of round 2 of yeast-display sorting.

This application relates to an improved screening method for the selection of target-binding proteins having desirable biophysical properties. The method combines mRNA display and yeast surface display in a way that takes advantage of the desirable attributes of both processes. First, mRNA display technology is used to screen a large library of nucleic acid-protein fusions having high design complexity. Typically, the mRNA display phase of the selection method lasts for two to ten rounds and focuses on the removal of variants that do not bind the target of interest with desirable affinity. Once the population of variants has been reduced to a desired level of complexity, it is transferred to a yeast surface display system, which proceeds for additional rounds of screening. The yeast surface display phase of the selection method is designed to introduce selection stringency for a high display level, and thus selects target-binding candidates with high stability, high protein expression, proper folding, and low levels of aggregation. Accordingly, the screening methods disclosed herein are advantageous, in part, because (i) the mRNA display phase permits the screening of large libraries, thus increasing the probability of capturing target-binding protein variants having the desired target binding affinity, and (ii) the yeast surface display phase removes the variants with poor biophysical properties. Thus the odds of selecting a variant protein having the desired biophysical and binding properties are higher when using the combination method disclosed herein than when using mRNA display technology or yeast display on its own.

The methods described herein may be used to isolate any type of binding protein that is compatible with mRNA display and yeast display. In certain embodiments, the binding proteins are small, single chain polypeptides. Exemplary binding proteins that can be selected using the methods described herein include, for example, scFv proteins, Fab proteins and $^{10}$Fn3 domain proteins.

The methods described herein may be used to isolate a binding protein that binds to any target of interest. Exemplary targets are therapeutic proteins, such as, for example, PCSK9, VEGFR2, IGF-1R, TNFα and EGFR. Proteins binding to such targets may be used in place of antibody therapeutics that bind to the same target. For example, proteins that bind to TNFα may be used to treat autoimmune disorders such as rheumatoid arthritis, inflammatory bowel disease, psoriasis, and asthma; proteins that bind to VEGFR2, IGF-1R, and EGFR may be used to treat hyperproliferative disorders or diseases associated with unwanted angiogenesis, such as cancers or tumors; and proteins that bind to PCSK9 may be used to treat atherosclerosis, hypercholesterolemia and other cholesterol related diseases. Alternatively, binding proteins selected using the methods described herein may be used to detect the target protein (either in vitro or in vivo, e.g., when fused to a detectable label) or to purify the target protein (e.g., by isolating the binding on a solid support such as a column resin).

In exemplary embodiments, a library is first screened using mRNA display. The library used for the mRNA display may contain at least $10^{10}$, $10^{11}$, $10^{12}$, $10^{13}$, $10^{14}$ or $10^{15}$ members, or from $10^{10}$ to $10^{15}$, $10^{10}$ to $10^{14}$, $10^{10}$ to $10^{12}$, $10^{11}$ to $10^{13}$, $10^{12}$ to $10^{14}$, or from $10^{12}$ to $10^{13}$ members. In certain embodiments, at least 2, 3, 4, 5, 6, 7, 8, 9 or 10 rounds of mRNA display screening is carried out, or from 2-10, 2-8, 2-7, 2-6, 2-5, 2-4, 2-3, 3-10, 3-8, 3-6, 3-5, 3-4, 4-10, 4-8, or 4-6 rounds of mRNA display screening is conducted. In certain embodiments, iterative rounds of mRNA display screening are carried out until the diversity of the library is simplified to less than about $10^{10}$, $10^9$, $10^8$, $10^7$, $10^6$, $10^5$, $10^4$ members, or from $10^5$-$10^{10}$, $10^5$-$10^8$, $10^5$-$10^7$, $10^5$-$10^6$ members. A round of mRNA display screening refers to contacting an immobilized target with the library, washing the mixture to remove unbound library members, and isolating the bound mRNA-protein fusion library members. The result of the mRNA display screening is a less diverse library that has been enriched for protein variants that bind to the desired target.

In exemplary embodiments, the enriched library of clones from mRNA display is then subjected to additional rounds of screening using a yeast surface display technique. The enriched library of clones may contain less than about $10^{10}$, $10^9$, $10^8$, $10^7$, $10^6$, $10^5$, $10^4$ members, or from $10^5$-$10^{10}$, $10^5$-$10^8$, $10^5$-$10^7$, $10^5$-$10^6$ members. In certain embodiments, at least 2, 3, 4, 5, 6, 7, 8, 9 or 10 rounds of yeast display screening are carried out, or from 2-10, 2-8, 2-7, 2-6, 2-5, 2-4, 2-3, 3-10, 3-8, 3-6, 3-5, 3-4, 4-10, 4-8, or 4-6 rounds of yeast display screening are conducted. In certain embodiments, iterative rounds of yeast display screening are carried out until the diversity of the library is simplified to less than about $10^4$, $10^3$, or $10^2$ members, or from $10^2$-$10^4$ or $10^2$-$10^3$ members. In certain embodiments, iterative rounds of yeast display are carried out until one or more protein variants having desired binding and biophysical characteristics are identified from the library. A round of yeast display screening refers to contacting yeast decorated with target binding proteins with a labeled target and selecting those yeast displaying protein variants that have a desired level of binding to the target. The result of the yeast display screening is the identification of one or more clones that bind to the target with a desired level of affinity and that have desirable biophysical properties such as thermostability, proper folding, little to no aggregation, and high levels of expression.

In certain embodiments, the library may be subject to affinity maturation at one or more times during the method. For example, gene shuffling and/or error-prone PCR may be applied during the mRNA display screening, the yeast display screening, or during both or between the two screening procedures in order to introduce additional diversity.

In certain embodiments, the methods described herein increase the likelihood of selecting a target binding protein having one or more desirable biophysical or biochemical properties, such as, for example, one or more of solubility, thermostability, high expression levels, low levels of aggregation, proper folding and/or binding specificity. In certain embodiments, the methods described herein increase the likelihood of selecting a target-binding protein variant that is monomeric by at least two-fold, three-fold, four-fold, five-fold, ten-fold or more, or from 2 to 5 fold, or from 2 to 3 fold relative to a method involving screening the same library using only mRNA display. In certain embodiments, the methods described herein result in the selection of a population of target binding protein variants having an average melting temperature (Tm) that is higher than the average melting temperature of the population of target binding protein variants selected by screening the same library using only mRNA display.

mRNA Display mRNA display is a mRNA-protein fusion technology that covalently couples a protein to its encoding genetic material. mRNA display technology may be used to generate large libraries that can contain as many as $10^{13}$ different variants. For a more detailed description of mRNA display technology see Szostak et al., U.S. Pat. Nos. 6,258,558, 6,261,804, 6,214,553, 6,281,344, 6,207,446, 6,518,018; PCT Publication Nos. WO 00/34784, WO 01/64942, WO 02/032925; and Roberts et al., *Proc Natl. Acad. Sci.*, 94:12297-12302 (1997), herein incorporated by reference.

Because an mRNA-display library is constructed exclusively in vitro, it can contain as many as $10^{13}$ different variants, two to five orders of magnitude higher than what is accessible to methods that require the transformation of a host microorganism. Suitable examples of cell-free protein synthesis systems that may be used in connection with mRNA display include, for example, wheat germ extract, rabbit reticulocyte lysate, or *Escherichia coli* S30 extract. Since $^{10}$Fn3 contains fewer than 100 amino-acid residues, the DNA segment encoding the library of $^{10}$Fn3 variants can be easily assembled by PCR from eight to twelve overlapped oligonucleotides, some of which contain randomized or partially diversified sequences. It may be advantageous to design the library-construction strategy so that the length of diversified oligonucleotides is minimized, to use the highest quality oligonucleotides available, and to assemble them using a high-fidelity polymerase. The amount of PCR primers and the number of cycles during the amplification of diversified library fragments and full-length library should be limited to obtain the desired number of copies of each clone, while limiting the number of unplanned mutations.

Once the library is assembled, it is then transcribed into mRNA using an in vitro transcription system. The mRNA is then chemically linked to a DNA oligonucleotide that contains a peptidyl adaptor molecule, such as the tRNA-like molecule puromycin, and subjected to an in vitro translation system. After the mRNA is translated into a polypeptide, the peptidyl acceptor molecule conjugated to the mRNA inserts into the ribosome and is added to the nascent polypeptide chain, as if it were the last amino-acid residue in the chain. The resulting covalent mRNA-protein fusion may be reverse transcribed to add a stabilizing, complimentary DNA strand. The mRNA-protein fusion molecules are purified away from the in vitro translation reaction mixture using any art-recognized methods of separation of mRNA-protein fusion molecules from a reaction mixture. In some embodiments, the mRNA-protein fusions are separated by chromatography using a polydeoxythimidine (polydT) resin. In certain embodiments, the mRNA-protein fusions are separated by binding to an antibody specific for an epitope present in the protein component of the mRNA-protein fusion. The epitope may be an amino acid sequence tag, for example, FLAG® or HA tags, incorporated into the amino acid sequence of the protein component of the mRNA-protein fusion, for example, at the N-terminal or C-terminal region.

A peptidyl acceptor refers to any molecule capable of being added to the C-terminus of a growing protein chain by the catalytic activity of the ribosomal peptidyl transferase function. Typically, such molecules contain (i) a nucleotide or nucleotide-like moiety (for example, puromycin and analogues thereof), (ii) an amino acid or amino acid-like moiety (for example, any of the 20 D- or L-amino acids or any amino acid analog thereof (for example, O-methyl tyrosine or any of the analogs described by Ellman et al., *Meth. Enzymol.*, 202:301 (1991)), and (iii) a linkage between the two (for example, an ester, amide, or ketone linkage at the 3' position or, less preferably, the 2' position); preferably, this linkage does not significantly perturb the structure of the ring from the natural ribonucleotide conformation. In addition, this term encompasses, without limitation, a peptide acceptor molecule that is covalently bonded (either directly or indirectly through intervening nucleic acid sequence) to the protein coding sequence, as well as one that is joined to the protein coding sequence by some non-covalent means, for example, through hybridization using a second nucleic acid sequence that binds at or near the 3' end of the protein coding sequence and that itself is bound to a peptide acceptor molecule.

In some embodiments, the peptidyl acceptor is a tRNA-like structure other than puromycin. Such compounds include, without limitation, any compound which possesses an amino acid linked to an adenine or an adenine-like compound, such as the amino acid nucleotides, phenylalanyl-adenosine (A-Phe), tyrosyl adenosine (A-Tyr), and alanyl adenosine (A-Ala), as well as amide-linked structures, such as phenylalanyl 3' deoxy 3' amino adenosine, alanyl 3' deoxy 3' amino adenosine, and tyrosyl 3' deoxy 3' amino adenosine; in any of these compounds, any of the naturally-occurring L-amino acids or their analogs may be utilized. In addition, a combined tRNA-like 3' structure-puromycin conjugate may also be used in the invention.

The library is then contacted with a target of interest. The selection process is carried out in an aqueous medium wherein parameters such as time, temperature, pH, buffer, salt concentration, and detergent concentration may be varied according the stringency of the selection strategy employed.

To enrich an mRNA-displayed library of protein variants for those that bind the target of interest, the library is incubated with the target. Typically, the target molecule is captured on a solid surface such as a bead. In some embodiments, a capturable moiety is present on the target molecule and is used to immobilize the target on bead. The capturable moiety may be biotin, an Fc domain, a purification tag, or any other capturable moiety known to those skilled in the art. The beads may be coated with streptavidin, protein A, or tag-specific antibody, or any other agent that will capture the capturable-moiety. After the mRNA-displayed library is incubated with the bead-captured target, the mRNA-displayed molecules that bind to the target remain associated with the bead-captured target, and the non-binding molecules are removed as flow-through and wash. Alternatively, the target can be conjugated directly to a solid support. Exemplary solid supports include, for example, an epoxy resin, an agarose column, a SEPHAROSE® column, or a BIACORE® chip. The mRNA-display library is then mixed with the immobilized target, and the reaction is washed, leaving the target-bound variants bound to the immobilized target. In either case, concentrated base is added to degrade the mRNA, thereby releasing the DNA encoding the proteins variants that bound to the target. High-fidelity PCR is used to amplify the captured DNA, now enriched for sequences encoding target-binding variants. The enriched population is ready to be transcribed, conjugated to an acceptor molecule, translated, and introduced into the next round of selection. The mRNA-display selection cycle is typically repeated for at least 4 to 6 rounds in order to select/enrich those fusion molecules comprising polypeptide sequences exhibiting affinity for the target material.

Once an enriched population of mRNA-displayed protein variants shows detectable binding to target under conditions of desired stringency, the encoding DNAs may be purified and subsequently PCR-amplified using a high fidelity polymerase. The DNA fragments may be sequenced and the variants of interest may be cloned into an expression vector, expressed in a suitable expression system, for example, a bacterial, yeast, insect or mammalian system, purified as protein, and characterized. At this point, the DNA encoding the variants that bind the target with high affinity may also be transferred to the yeast surface display system detailed below.

In some embodiments, measures are taken to avoid selecting protein variants that bind to components of the system other than the target, for example, to the capture beads or streptavidin. This can be achieved by subjecting each population of mRNA-protein fusions to at least one round of fake selection, or "pre-clear", which consists of incubating the library with all the system components except the target molecule. It may also be advantageous to alternate the target capture format. For example, each odd-numbered round may employ biotinylated target and streptavidin beads, and each even-numbered round may employ epoxy-immobilized target.

Yeast Surface Display

Yeast surface display is a powerful genetic method that can be used to select proteins with increased or decreased affinity for another molecule, altered specificity, or conditional binding. The genetic malleability of yeast, the ease of growth of this microbe, and the ability to modify binding conditions in vitro combine to produce unprecedented control over the engineering of affinity and specificity. A library of protein variants are displayed on the surface of yeast cells by genetic fusion with yeast secretory and/or anchor proteins in a form accessible for binding to macromolecules, and selected on the basis of binding characteristics using fluorescence activated cell sorting (FACS). In certain embodiments, yeast-displayed proteins are labeled by dyes that fluoresce at two different frequencies. The first dye is conjugated or non-covalently associated with the target of interest; the intensity fluorescent signal at its frequency serves as a measure of the propensity of the displayed protein to bind the target. The second dye is conjugated to an antibody that recognizes an epitope tag that is a part of the displayed protein; the intensity fluorescent signal at its frequency serves as a measure of the amount of the protein that is displayed on the yeast cell.

Yeast surface display offers advantages over bacteria-based technologies (e.g., phage-display) or mRNA display in that yeast can process proteins that require endoplasmatic reticulum (ER)-specific post-translational processing for efficient folding and activity. An additional benefit of yeast surface display is that the protein to be displayed must pass through the ER and the rest of cellular secretory machinery for assembly and transport to the cell surface. The efficiency of secretion (and thus of display) of a protein depends of the protein biophysical properties, with unstable or aggregation-prone proteins being preferentially removed from the pathway before they reach the cell surface (e.g., reference: Hackel et al., *J. Mol. Biol.*, 401:84-96 (2010)). Therefore, yeast surface display provides the advantage of selecting and isolating polypeptides possessing a variety of desirable characteristics (e.g., thermal stability, desirable expression levels, properly folded, non-aggregating) in addition any other improvement that is selectable via surface expression of a displayed polypeptide (e.g., target binding, specificity, selectivity). As a consequence, a FACS-gating strategy that only captures the yeast cells with the very highest (e.g., the top 5%, the top 2%, the top 1%, or the top 0.1%) intensity of the fluorescent signal associated with the display level will lead to the selection of the proteins with the highest stability and solubility from the mixture.

Any means to display a protein on the surface of yeast is encompassed by the present disclosure. The different yeast surface display methods all provide a means of tightly linking each protein encoded by the library (phenotype) to the yeast cell which carries the plasmid encoding that protein (genotype). Any stable linkage between phenotype and genotype will allow the use of yeast surface display in conjunction with mRNA display. Most yeast display methods described to date use the yeast *Saccharomyces cerevisiae*, but other yeast species, for example, *Pichia pastoris*, could also be used. There are three commonly used *S. cerevisiae* based yeast surface display methods: the Aga2-based, the Aga1-based, and the biotin-based surface display methods.

In Aga2-based yeast surface display, a protein, or a library of protein variants, is genetically fused to a yeast protein, agglutinin a 2 (Aga2), which is naturally associated with yeast cell wall, and to an epitope tag such as, for example, c-myc or HA. Typically, the arrangement of the fusion protein is Aga2-protein variant-tag, but different arrangements have been described. The gene encoding the fusion may be controlled by an inducible promoter, such as, for example, the galactose-inducible promoter, GAL1-10. Upon induction, the gene product is secreted from the cell in complex with agglutinin-a-1 (Aga1), with which it forms two disulfide bonds. The Aga1, a natural cell wall protein, is retained in the yeast cell wall, and thus anchors the Aga2-protein variant fusion to the cell wall also. The result is a culture where each yeast cell displays between 10,000 and 100,000 copies of a single protein variant.

In Aga1-based yeast surface display, a protein, or a library of protein variants, is genetically fused to a different natural yeast cell-wall protein, agglutinin alpha 1 (Aga1), and to an epitope tag such as, for example, c-myc or HA. The gene encoding the fusion may be controlled by an inducible promoter, such as, the galactose-inducible promoter, GAL7. As in Aga2-based yeast surface display, fusion proteins are expressed in the presence of galactose, secreted from the yeast cells, and retained on the surface of the yeast cells.

In certain embodiments, a method that relies on in vivo biotinylation of the protein to be displayed, followed by its capture on the yeast cell surface is used. For example, the protein to be displayed is genetically fused to a yeast secretory protein of choice and to a biotin-acceptor peptide (BAP). An epitope tag, such HA or FLAG®, is also engineered immediately downstream from the sequence encoding the protein variant. Common secretory proteins include yeast alpha mating factor prepro 1 (WTαMFpp), the invertase leader, synthetic leaders (Clements et al., *Gene*, 106: 267-271 (1991)), and the engineered alpha mating factor prepro αMFpp8 (Rakestraw et al., *Biotechnol. Bioeng.*, 103:1192-1201 (2009)). The gene encoding the fusion may be controlled by an inducible promoter, such as, for example, the galactose-inducible promoter, GAL1-10. Before inducing expression of the protein to be displayed, the outside surface of the yeast cell is chemically conjugated to avidin. Upon induction, the biotin-acceptor peptide in the fusion protein is biotinylated inside the cell by a co-expressed biotin ligase. The biotinylated fusion protein is then secreted from the cell and captured on the cell-surface avidin due to the extremely high-affinity interaction between avidin and biotin.

In certain embodiments, the protein variants to be displayed are genetically fused to a GPI (Glycosyl-Phosphatidyl-Inositol) anchor protein, such as the mating type protein agglutinin-a-1 (Aga1), flocculin proteins (e.g., Flo1), as well as Sed1, Cwp1, Cwp2, Tip1 and Tir1/Srp1. In certain embodiments, the anchor protein is selected from the group consisting of a GPI anchor, a modified GPI anchor, a major cell wall protein, CCW14, CIS3, CWP1, PIR1, and PIR3.

In order to identify and capture the yeast cells that display protein variants with desired properties, the yeast culture is incubated with the target of interest, then simultaneously labeled by two sets of reagents: the first set detects the target, and the second set detects the protein variant. The target and protein variant may be detected using the engineered capture feature. For example, a biotinylated target can be detected with streptavidin conjugated with a fluorescent dye, or an Fc fusion can be detected with an anti-Fc specific antibody conjugated to a fluorescent dye. Typically the protein variant is also detected using a fluorescently labeled antibody specific for the epitope tag fused to the protein variant. When using antibodies as detection reagents, the fluorescent antibody may bind directly to the target, fusion protein, or tag, or an unlabeled primary antibody may bind to the target, protein variant, or tag, and the primary antibody is then bound by a labeled secondary antibody. The detection reagents directed at the target and at the protein variant are chosen such that they fluoresce at different wavelengths. As the labeled yeast cells are passed through a fluorescence-activated cell sorter (FACS), the intensity of signal at each of the two wavelengths is measured for each cell. The user then defines the signal range for each wavelength ("the gate") for which yeast cells are captured; the rest of the culture is discarded. The captured cells are re-grown, re-labeled, and re-sorted; typically, between four and eight sorts are required to for the population to converge on a small number of the most successful variants.

In an alternative embodiment, a first fluorescent protein is engineered immediately downstream from the sequence encoding the protein variant (e.g., GFP, YFP, etc.). The target protein may also be engineered to be fused to a second protein that fluoresces at a different wavelength than the first. FACS may then be used to identify and sort the captured yeast cells without the need for the use of labeled detection reagent.

Once an enriched population of yeast-displayed protein variants shows detectable binding to target under conditions of desired stringency, single cell clones can be isolated and characterized in several, complementary methods. When the primary goal is to identify clones with the desired binding affinity and specificity, clones can be isolated by growth on an agar plate followed by small-scale growth in deep-well microplates. For example, accurate estimates of the dissociation constant (Kd) can be determined by labeling the yeast cells with a series of different concentrations of target followed by analytical flow cytometry. Similarly, the off-rate of a particular variant can be measured by labeling the clonal culture with labeled target, incubating with excess unlabeled target, and using analytical flow cytometry to determine the fraction of target still bound to yeast at different time points. The identity of the protein variants with desired properties can readily be determined by PCR amplification of the DNA encoding those protein variants from yeast colonies.

When it is necessary to perform more complex assays such as cell-based functional assays and assays for characterizing biophysical properties, purified proteins are produced in a small scale. In cases like these, it may be advantageous that the starting yeast surface display DNA library be expressed in a shuttle plasmid, i.e., a plasmid that can propagate in both yeast and bacteria. Preferably, the shuttle plasmid can propagate in *Saccharomyces cerevisiae* and *Escherichia coli*. In some embodiments, the shuttle-plasmid is extracted from the yeast (e.g., using the Zymoprep yeast Plasmid Miniprep II kit by Zymo Research, Irvine, Calif.) and transferred to *E. coli*. Individual *E. coli* clones are sequenced to identify unique selected clones and their level of enrichment. The selected clones of interest can be expressed in an expression system of interest and purified using methods well know in the art. The purified variant proteins of interest can then be further characterized.

Affinity Maturation

Once a target-binding protein has been selected by mRNA display and/or yeast display, the properties of such a clone can be further optimized by a process named affinity maturation. In affinity maturation, the sequence of the gene encoding a lead protein is re-diversified to an intermediate degree, still retaining some of the sequence characteristics of the parent clone but also introducing additional diversity. Error-prone PCR and DNA shuffling are two of the many possible ways of introducing into the sequence such additional diversity. For example, after one or more rounds of selection, PCR can be used to incorporate mutations in the DNA sequences encoding the protein variants that bind the target of interest. The process, also known as affinity maturation, is typically repeated for several cycles in order to obtain the peptides having improved affinity for the target material. Alternatively, gene shuffling may be employed to swap different binding regions within the protein variants. For examples, gene shuffling can be used in connection with a library of $^{10}$Fn3 variants to mix and match BC, DE and/or FG loops from different protein variants that have been selected to bind to the same target. In certain embodiments, affinity maturation may be used following at least one round of mRNA display screening, following at least one round of yeast display screening, or both. In certain embodiments, affinity maturation is used after selecting a population of target binding protein variants using mRNA display before transitioning the binding protein variants into the yeast display system. In certain embodiments, at the end of the process, e.g., after suitable binding proteins have been isolated using repeated rounds of mRNA display followed by repeated rounds of yeast display.

Polypeptides Comprising $^{10}$Fn3 Domains

In some embodiments, the target binding protein is a $^{10}$Fn3 domain-based protein. Fibronectin based scaffold proteins generally make use of a scaffold derived from a fibronectin type III (Fn3) or Fn3-like domain and function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies. An example of fibronectin-based scaffold proteins are ADNECTINS™ (Adnexus, a wholly owned subsidiary of Bristol-Myers Squibb). Fibronectin-based scaffold proteins and ADNECTINS™ may be monovalent or multivalent.

An Fn3 domain is small, monomeric, soluble, and stable. It lacks disulfide bonds and, therefore, is stable under reducing conditions. The overall structure of Fn3 resembles the Ig fold. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face and loops BC, DE, and FG are located on the opposing face. Any or all of loops AB, BC, CD, DE, EF and FG may participate in ligand binding. There are at least 15 different modules of Fn3, and while the sequence homology between the modules is low, they all share a high similarity in tertiary structure.

The amino acid sequence of the naturally occurring human tenth fibronectin type III domain, i.e., the tenth module of human Fn3 ($^{10}$Fn3), is set forth in SEQ ID NO: 1:

(SEQ ID NO: 1)
*VERSUSDVPRDL*EVVAAT<u>PTSLLI</u>SWDAPAVTVRYYRITYGET<u>GGNSPV</u>
QEFTVPGSKST ATI<u>SGLKPGV</u>DYTITVYAVTGRGDSPASSKPISINYRT (the AB, CD and EF loops are underlined, and the BC, FG, and DE loops are emphasized in bold).

In SEQ ID NO:1, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87. See e.g., Xu et al., *Chemistry & Biology*, 9:933-942 (2002). The BC, DE and FG loops align along one face of the molecule (sometimes referred to as the "north pole" loops) and the AB, CD and EF loops align along the opposite face of the molecule (sometimes referred to as the "south pole" loops). In SEQ ID NO: 1, beta strand A corresponds to residues 9-14, beta strand B corresponds to residues 17-20, beta strand C corresponds to residues 31-38, beta strand D corresponds to residues 46-50, beta strand E corresponds to residues 57-59, beta strand F corresponds to residues 67-75, and beta strand G corresponds to residues 88-94. The strands are connected to each other through the corresponding loop, e.g., strands A and B are connected via loop AB in the formation of strand A, loop AB, strand B, etc. The first 8 amino acids of SEQ ID NO:1 (italicized above) may be deleted while still retaining binding activity of the molecule. Residues involved in forming the hydrophobic core (the "core amino acid residues") include the amino acids corresponding to the following amino acids of SEQ ID NO: 1: L8, V10, A13, L18, I20, W22, Y32, I34, Y36, F48, V50, A57, I59, L62, Y68, I70, V72, A74, I88, I90 and Y92, wherein the core amino acid residues are represented by the single letter amino acid code followed by the position at which they are located within SEQ ID NO: 1. See e.g., Dickinson et al., *J. Mol. Biol.*, 236:1079-1092 (1994).

$^{10}$Fn3 domains are structurally analogous to antibodies, specifically the variable region of an antibody. While $^{10}$Fn3 domains may be described as "antibody mimics" or "antibody-like proteins", they do offer a number of advantages over conventional antibodies. In particular, they exhibit better folding and thermostability properties as compared to antibodies, and they lack disulphide bonds, which are known to impede or prevent proper folding under certain conditions.

The BC, DE, and FG loops of $^{10}$Fn3 domains are analogous to the complementary determining regions (CDRs) from immunoglobulins. Alteration of the amino acid sequence in these loop regions changes the binding specificity of $^{10}$Fn3. $^{10}$Fn3 domains with modifications in the AB, CD and EF loops may also be made in order to produce a molecule that binds to a desired target. The protein sequences outside of the loops are analogous to the framework regions from immunoglobulins and play a role in the structural conformation of the $^{10}$Fn3. Alterations in the framework-like regions of $^{10}$Fn3 are permissible to the extent that the structural conformation is not so altered as to disrupt ligand binding.

As described above, amino acid residues corresponding to residues 21-30, 51-56, and 76-87 of SEQ ID NO: 1 define the BC, DE and FG loops, respectively. However, it should be understood that not every residue within the loop region needs to be modified in order to achieve a $^{10}$Fn3 binder having strong affinity for a desired target. For example, in many cases, only residues corresponding to amino acids 23-30 of the BC loop and 52-55 of the DE loop are modified and result in high affinity $^{10}$Fn3 binders. Accordingly, in certain embodiments, the BC loop may be defined by amino acids corresponding to residues 23-30 of SEQ ID NO: 1, and the DE loop may be defined by amino acids corresponding to residues 52-55 of SEQ ID NO: 1. Additionally, insertions and deletions in the loop regions may also be made while still producing high affinity $^{10}$Fn3 binders.

Libraries of $^{10}$Fn3 Domain-Based Proteins

Typically, the positions diversified in $^{10}$Fn3-based libraries comprise between one and three of the $^{10}$Fn3 loops that are structurally analogous to antibody complementarity-determining regions (CDRs), i.e., loops BC, DE, and FG, the intention being to generate contiguous surfaces for target recognition. Diversity is typically introduced into a library using synthetic oligonucleotides containing a mixture of nucleotides. The simplest and least expensive random oligonucleotides incorporate a random stretches of nucleotides that can encode any amino acid, such as the so-called NNK codon, where N is an equal mixture of A, T, G and C and K is a mixture of T and G. Alternatively, oligonucleotides synthesized from triphosphoramidite or ligated from double-stranded codons can be used to encode a biased amino-acid composition, for example, mimicking side-chain distribution in antibody CDRs. In addition to the loop sequence, loop length can be varied by incorporating into the library synthetic oligonucleotides of divergent lengths. The DNA library encoding the $^{10}$Fn3 variants may be designed to include a promoter (e.g., T7, SP6, T3) for in vitro transcription and a translation initiation sequence (e.g., Shine Dalgarno for E coli S30 extracts, Kozak sequence for eukaryotic systems) for in vitro translation, operably linked to the coding sequence. The construction of a library of variant $^{10}$Fn3 domains having sequence variations in each of the BC, DE and FG loops is described in Xu et al., *Chemistry & Biology*, 9:933-942 (2002). Libraries of molecules (e.g., molecules comprising one or more $^{10}$Fn3 domains or domains relating thereto) that may be screened are disclosed, e.g., WO 98/056915, WO 02/081497, WO 2008/031098; U.S. Publication No. 2003/186385; WO 2009/102421, WO 2009/142773, WO 2010/060095; U.S. Pat. Nos. 6,818,418, 6,673,901, 7,115,396; WO 2010/0273261, WO 2011/103105, WO 2011/130354, WO 2011/140086, WO 2011/150133, WO 2010/051274, WO 2010/051310, WO 2009/086116, WO 2009/086116, WO 2010/093627, WO 2011/137319, WO 2012/016245, WO 98/056915, WO 02/081497, WO 2008/031098; U.S. Publication No. 2003/186385; WO 2011/130324, WO 2011/130328, WO 2009/083804, WO 2009/133208, WO 2010/093627, WO 2011/051333, WO 2011/051466, and WO 2011/092233.

To create a library of mRNA-protein fusions for mRNA display, the RNA portion of an RNA-protein fusion may be chemically synthesized using standard techniques of oligonucleotide synthesis. Alternatively, the RNA portion may be generated by in vitro transcription of a DNA template. Various RNA polymerases may be used to generate the RNA strand including, for example, the SP6, T3 and *E. coli* RNA polymerases. In one preferred approach, T7 polymerase is used to enzymatically generate the RNA strand. In addition, the synthesized RNA may be, in whole or in part, modified RNA. In one particular example, phosphorothioate RNA may be produced (for example, by T7 transcription) using modified ribonucleotides and standard techniques. Such modified RNA provides the advantage of being nuclease stable.

To generate the RNA-protein fusions, any in vitro or in situ translation system may be utilized including, for example, eukaryotic translation systems from lysates from yeast, ascites, tumor cells (Leibowitz et al., *Meth. Enzymol.*, 194:536 (1991)), and *xenopus* oocyte eggs, and in vitro translation systems from bacterial systems, such as, those described in Zubay (*Ann. Rev. Genet.*, 7:267 (1973)); Chen et al. (*Meth. Enzymol.*, 101:44 (1983)); and Ellman (*Meth. Enzymol.*, 202:301 (1991)). Eukaryotic in vitro translation systems are preferred, including, for example, the wheat germ and reticulocyte lysate systems. In principle, however, any translation system which allows formation of an RNA-protein fusion and which does not significantly degrade the RNA portion of the fusion may be used. In addition, to reduce RNA degradation in any of these systems, degradation-blocking antisense oligonucleotides may be included in the translation reaction mixture; such oligonucleotides specifically hybridize to and cover sequences within the RNA portion of the molecule that trigger degradation (see, for example, Hanes et al., *Proc. Natl. Acad. Sci. USA*, 94:4937 (1997)).

To transition from the mRNA-display system to the yeast display system, the nucleic acid sequence isolated from the mRNA display screening are amplified using 5' and 3' primers that introduce sequence overlaps with the yeast-display plasmid. These sequences are then electroporated into yeast concurrently with the yeast display plasmid and the protein variant sequences are incorporated into the yeast display plasmids by homologous recombination.

Expression vectors suitable for use in generating the yeast surface display library may comprise, in a 5' to 3' direction, a eukaryotic promoter, a signal anchor or secretory domain of a protein, and a nucleotide sequence that is a cloning site, which allows insertion of a gene or gene fragment. Expression vectors for eukaryotic host cells typically include (i) eukaryotic DNA elements that control initiation of transcription, such as a promoter, (ii) eukaryotic DNA elements that control the processing of transcripts, such as a transcription termination/polyadenylation signal sequence, and (iii) optionally, eukaryotic DNA elements that control replication in the eukaryotic host cell if the vector is to be independently replicated (e.g., non-integrating vectors). Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. To ease construction of such expression vectors, the vectors may optionally include (iv) prokaryotic DNA elements coding for a bacterial replication origin and an antibiotic resistance marker to provide for the growth and selection of the expression vector when manipulating the vector in the bacterial host cell. Appropriate eukaryotic expression vectors for use with fungal, yeast, and mammalian cellular hosts are known in the art, and are described in, for example, Powels et al. (*Cloning Vectors: A Laboratory Manual*, Elsevier, NY (1985)). Yeast cloning vectors that may be adapted for use in surface display techniques include YIp-based vectors, such as YIp5, YRp vectors, such as YRp17, YEp vectors such as YEp13 and YCp vectors, such as YCp19. Yeast species that are suitable for surface display techniques include *Saccharomyces cerevisiae*, *Pichia pastoris*, and *Pichia methanolica*.

EXAMPLES

The invention now being generally described will be more readily understood by reference to the following examples which are included merely for purposes of illustration of certain aspects and embodiments of the present invention, and are not intended to limit the invention in any way.

Example 1

Selection and Characterization of PCSK9-Binding $^{10}$Fn3 Domain Proteins Having Favorable Biophysical Properties To evaluate the benefit of combining mRNA display and yeast surface display, PCSK9-binding proteins were selected from a $10^{12}$-membered library of variants of the $^{10}$Fn3 domain. Two different selection strategies were applied to the library in parallel:

1. mRNA display only ("R"). In this approach, the population was submitted to five consecutive rounds of mRNA display, all of which were performed at the PCSK9 target concentration of 100 nM. Nucleic-acid mixtures obtained after round 5 were subcloned into the *E. coli* vector pET9d. Approximately 2,100 clones were sequenced, and approximately 1,300 unique clones were expressed in *E. coli* and screened for PCSK9 binding. For this study, 89 of the 934 PCSK9-binding $^{10}$Fn3-based proteins were evaluated for state of aggregation and thermostability.

2. mRNA display followed by yeast surface display ("R+Y"). In this approach, the population that had undergone the first three rounds of mRNA-display selection described under (1) was transferred into a yeast surface display system, and subjected to five rounds of yeast surface display, also at the target concentration of 100 nM of PCSK9. The sorting criteria in yeast surface display are illustrated in FIG. 1, which shows the gates applied to labeled yeast surface populations in round 1. After each round of yeast surface display, plasmid DNA was extracted from the enriched culture; the $^{10}$Fn3 domain-encoding sequence was subcloned from the yeast-display plasmid into the *E. coli* vector pET9d, and 96 clones per round were sequenced. All clones enriched to more than 1% of the population after round 4 or round 5 were expressed in *E. coli* and screened for PCSK9 binding, state of aggregation, and thermostability. In addition, 20% of the clones that were detected by sequencing, at any frequency, in rounds 2 to 5 were also screened for the same properties.

When comparing approaches R and R+Y, the main focus was on two biophysical properties of the enriched clones:

1. State of association as determined by analytical size-exclusion chromatography. The size-exclusion chromatography trace of each $^{10}$Fn3-based protein was scored with a single number ("SEC score") according to the following criteria:
  a. SEC score 1: All monomeric,
  b. SEC score 2: Mostly monomeric, detectable amount of oligomer,
  c. SEC score 3: Mostly oligomeric, detectable amount of monomer, and
  d. SEC score 4: Mostly aggregated.

2. Melting temperature ($T_m$) as determined by differential scanning calorimetry. Only $^{10}$Fn3 domain proteins with SEC scores of 1, 2, or 3 were subjected to differential scanning calorimetry.

Figure 2:
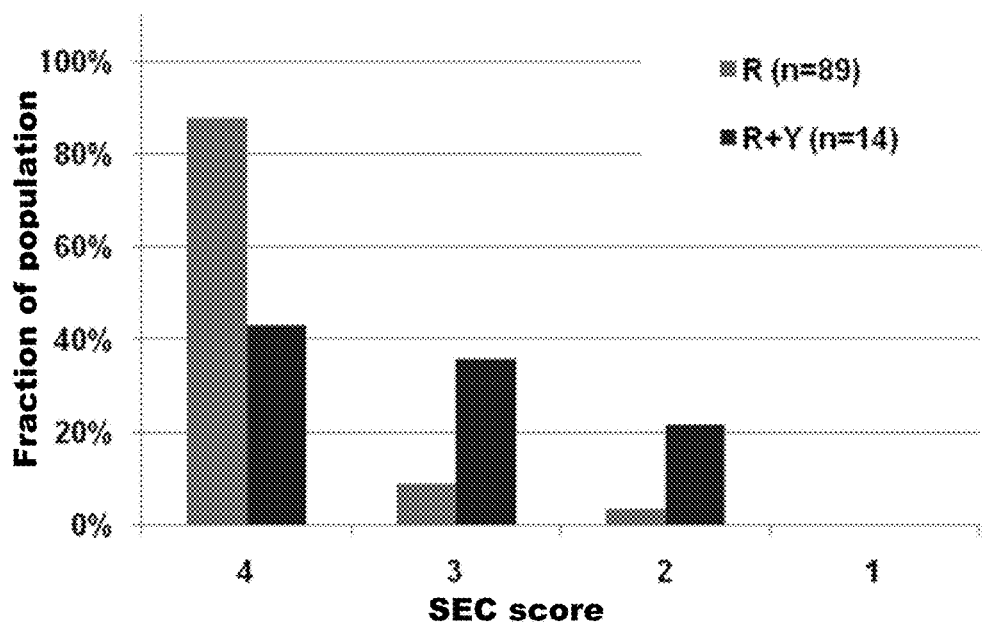
FIG. 2. Comparison of state of aggregation between $^{10}$Fn3 domain protein populations selected for binding to PCSK9 by mRNA display only ("R"; left bar of each double bar) versus by combination of mRNA display and yeast surface display ("R+Y"; right bar of each double bar). The proteins scored as "4" are predominantly aggregated, the proteins scored as "3" are a mixture of oligomer and monomer, and the proteins scored as "2" are mostly monomeric, with a minor fraction of oligomer. None of the proteins tested were completely monomeric.

The comparison of SEC scores between the two populations (FIG. 2) shows that the combined (R+Y) approach led to an approximately two-fold decrease relative to mRNA display only (R) in the fraction of highly aggregated $^{10}$Fn3 domain proteins (SEC score 4), to a four-fold increase in fraction of mostly oligomeric $^{10}$Fn3 domain proteins with some monomer, and to a seven-fold increase in fraction of mostly monomeric $^{10}$Fn3 domain proteins. Given that the monomeric state is preferred in protein therapeutics, this data demonstrates that the addition of yeast surface display to mRNA display can increase the efficiency of drug discovery.

Figure 3:
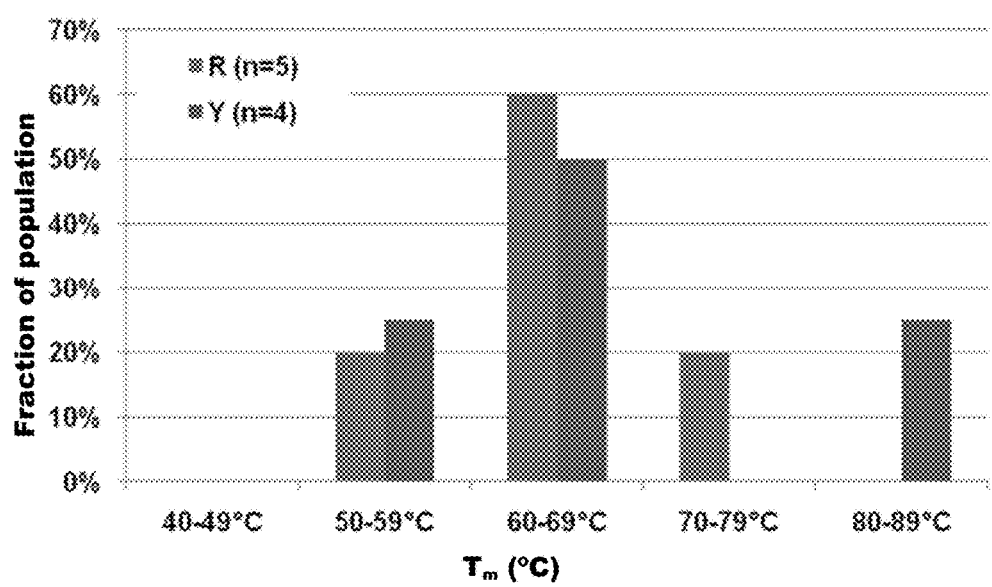
FIG. 3. Comparison of thermostability between $^{10}$Fn3 domain protein populations selected for binding to PCSK9 by mRNA display only ("R"; left bar of each double bar) versus by combination of mRNA display and yeast surface display ("Y"; right bar of each double bar). Melting temperatures ("$T_m$") were determined by differential scanning calorimetry.

The difference in $T_m$ values between the two populations (FIG. 3) is smaller and harder to interpret due to a small number of clones tested. Nevertheless, the identification of a new $^{10}$Fn3 domain protein with a melting temperature of 87° C. using the (R+Y) approach also suggests that the use of a combination of mRNA display and yeast surface display is preferable to the use of mRNA display alone.

Example 2

Selection and Characterization of $^{10}$Fn3 Domain Proteins Binding a Protein Target and Having Favorable Biophysical Properties To evaluate the benefit of combining mRNA display and yeast surface display, proteins binding to a target protein, which is different from that in Example 1, were selected from a $10^{12}$-membered library of variants of the $^{10}$Fn3 domain. Two different selection strategies were applied to the library in parallel:

1. mRNA display only ("R"). In this approach, the population was submitted to five consecutive rounds of mRNA display, all of which were performed at the target concentration of 100 nM. Nucleic-acid mixtures obtained after rounds 2 and 3 were subcloned into the *E. coli* vector pET9d and evaluated for state of aggregation and thermostability.

Figure 4:
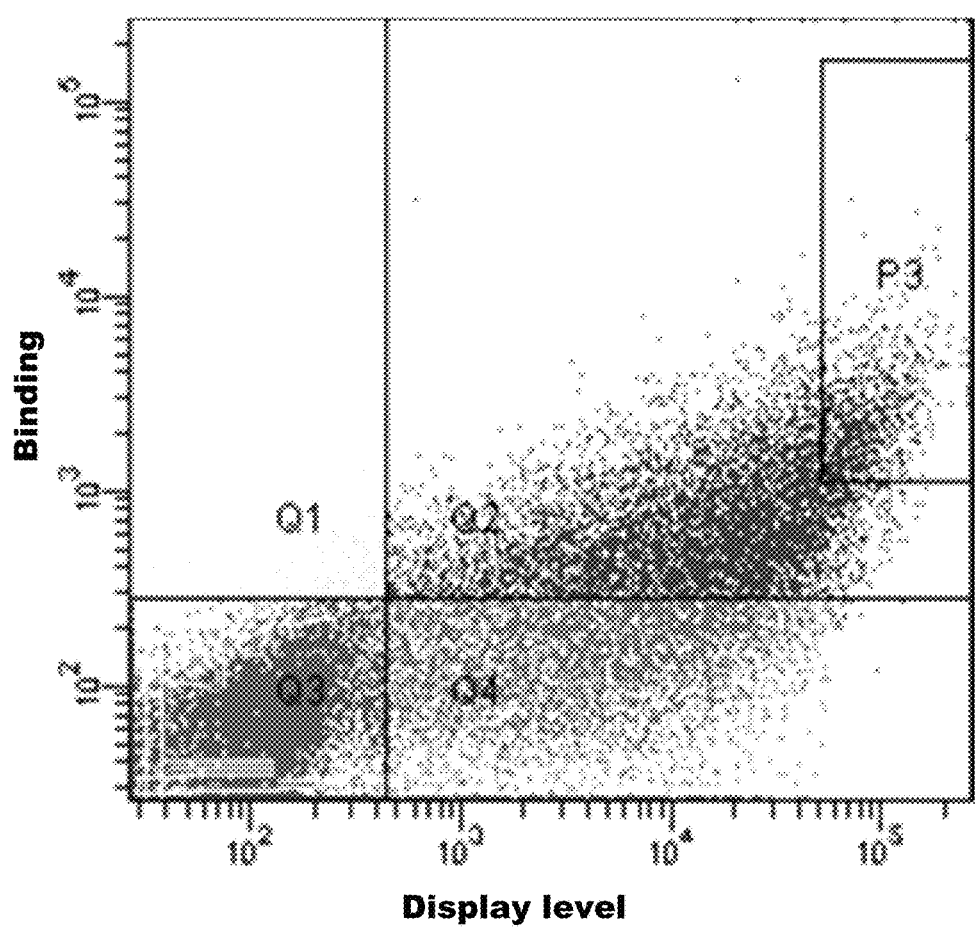
FIG. 4. Yeast population labeled in round 3 of yeast surface display. Relative "Display level" is revealed by fluorescent labeling of the C-terminal epitope tag, and "Binding" is quantified by labeling with fluorescently labeled target. The gate labeled "P3" contains yeast cells that are decorated with $^{10}$Fn3 domain proteins that both display at a high level and bind the target; the cells in this gate were captured by fluorescence-activated cell sorting and used as the starting point of round 4 of yeast-display sorting.

2. mRNA display followed by yeast surface display ("R+Y"). In this approach, the population that had undergone the first two and the first three rounds of mRNA-display selection described under (1) was transferred into a yeast surface display system, and subjected to five rounds of yeast surface display. The first round of sorting was performed for display level only, and rounds 2 to 5 were performed at the target concentration of 100 nM. The sorting criteria in yeast surface display are illustrated in FIG. 4, which shows the gates applied to labeled yeast surface populations in round 3. After rounds 3, 4, and 5 of yeast surface display, plasmid DNA was extracted from the enriched culture; the $^{10}$Fn3 domain-encoding sequence was subcloned from the yeast-display plasmid into the *E. coli* vector pET9d, sequenced, expressed in *E. coli* and screened for target binding, state of aggregation, and thermostability.

When comparing approaches R and R+Y, the main focus was on two biophysical properties of the enriched clones:

1. State of association as determined by analytical size-exclusion chromatography. The size-exclusion chromatography trace of each $^{10}$Fn3-based protein was scored with a single number ("SEC score") according to the following criteria:

a. SEC score 1: All monomeric,
b. SEC score 2: Mostly monomeric, detectable amount of oligomer,
c. SEC score 3: Mostly oligomeric, detectable amount of monomer, and
d. SEC score 4: Mostly aggregated.

2. Melting temperature (half point of thermal transition; $T_H$) as determined by fluorescence-detected thermal denaturation, where the temperature at the half-point of the denaturing thermal transition was recorded.

Figure 5:
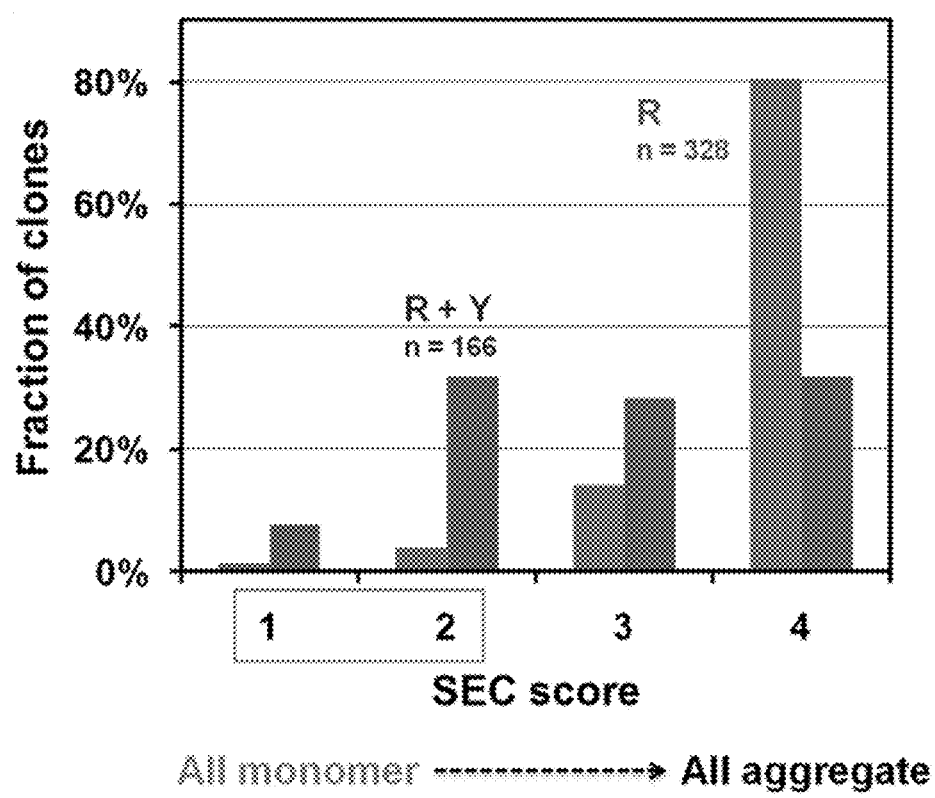
FIG. 5. Comparison of state of aggregation between $^{10}$Fn3 domain protein populations selected for binding to the target by mRNA display only ("R"; left bar of each double bar) versus by combination of mRNA display and yeast surface display ("R+Y"; right bar of each double bar). The proteins scored as "4" are predominantly aggregated, the proteins scored as "3" are a mixture of oligomer and monomer, the proteins scored as "2" are mostly monomeric, with a minor fraction of oligomer, and proteins scored as "1" are completely monomeric.

The comparison of SEC scores between the two populations (FIG. 5) shows that the combined (R+Y) approach led to a 2½-fold decrease relative to mRNA display only (R) in the fraction of highly aggregated $^{10}$Fn3 domain proteins (SEC score 4); an 8 fold increase relative to the mRNA display only in the fraction of all monomeric protein (SEC score 1); an 8 fold increase relative to the mRNA display only in the fraction of mostly monomeric protein (SEC score 2); and a 2 fold increase relative to the mRNA display only in the fraction of mostly oligomeric protein (SEC score 3). Given that the monomeric state is preferred in protein therapeutics, this data again demonstrates that the addition of yeast surface display to mRNA display can increase the efficiency of drug discovery.

Figure 6:
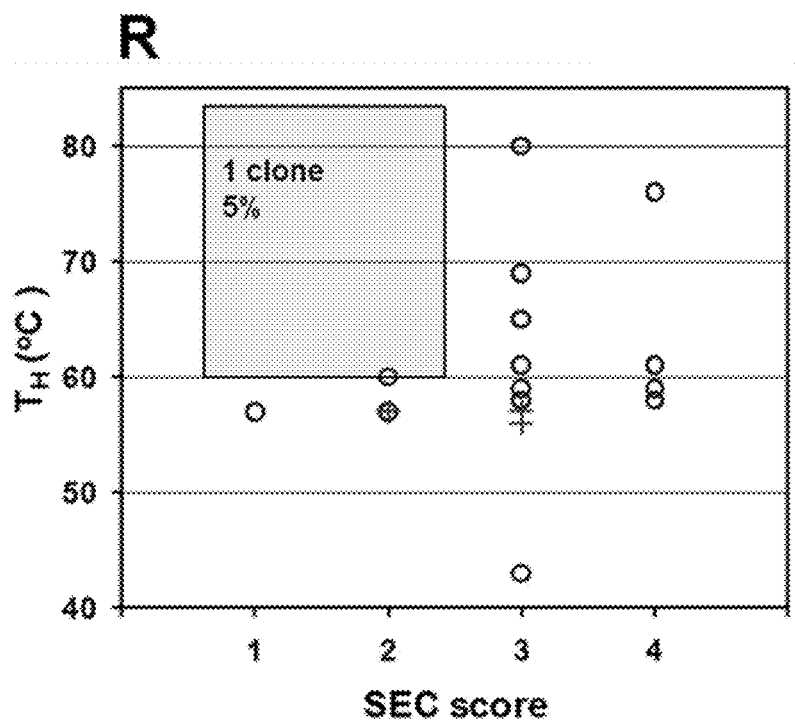
FIG. 6. Comparison of thermostability and state of aggregations between $^{10}$Fn3 domain protein populations selected for binding to the target by mRNA display only ("R") versus by combination of mRNA display and yeast surface display ("Y"). Half-points of thermal transition ("$T_H$") were monitored by change in fluorescence upon heating.
Figure 6:
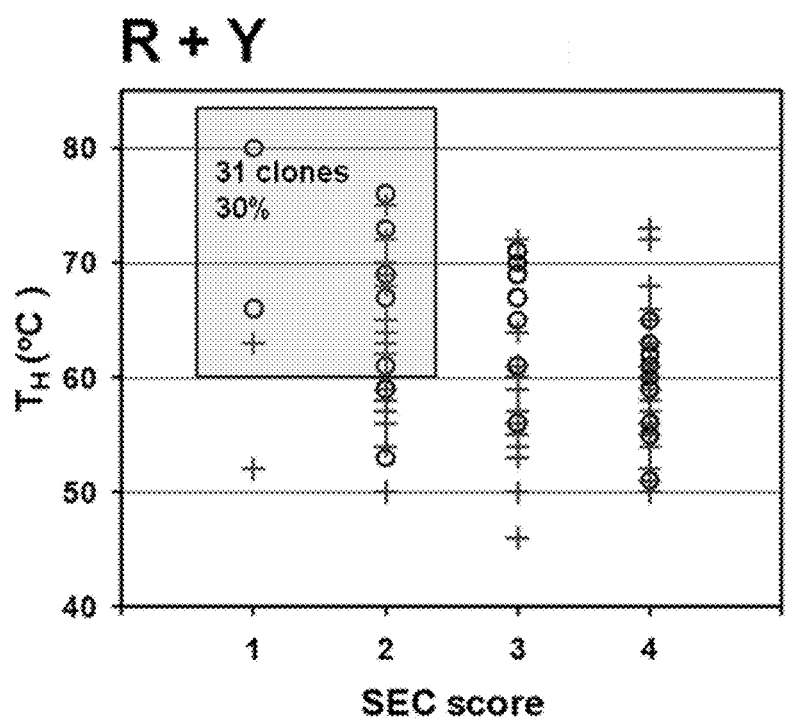

In this case, the difference in $T_H$ values between the two populations (FIG. 6) is as dramatic as the difference between their propensity to aggregate. Particular attention is drawn to the region in the boxed area, which highlights the proteins with both a high melting temperature (higher or equal to 60° C.) and a completely or mostly monomeric state (SEC score 1 or 2). Proteins in this region represent the most promising drug candidates; the addition of yeast surface display to the selection protocol increased their number 30 fold.

INCORPORATION BY REFERENCE

The entire disclosure of each document cited (including patents, patent applications, journal articles, abstracts, laboratory manuals, books, GENBANK® Accession numbers, SWISS-PROT® Accession numbers, or other disclosures) in the Background, Detailed Description, Brief Description of Drawings, and Examples is hereby incorporated herein by reference in their entirety.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

I claim:

1. A method for selecting a target-binding protein with favorable biophysical properties comprising
    (i) selecting a first population of target-binding protein variants consisting of at most $10^3$ target-binding protein variants from a library comprising at least about $10^{12}$ protein variants using mRNA display, comprising conducting a number of rounds of selection sufficient to obtain the at most $10^3$ target-binding protein variants, wherein the library of protein variants is a library of the 10th domain of fibronectin type III ($^{10}$Fn3) variants;
    (ii) determining whether a significant number of the at most $10^3$ target-binding protein variants have favorable biophysical properties, wherein the favorable biophysical properties are one or more of solubility, thermostability, high expression levels, low levels of aggregation, proper folding and binding specificity; and (iii) if a significant number of the at most $10^3$ target-binding protein variants do not have favorable biophysical properties, then selecting a population of at most $10^3$ target-binding protein variants from at least $10^5$ target-binding protein variants obtained during the selection in step (i) using yeast surface display.

2. The method of claim 1, wherein selecting a population of at least $10^3$ target-binding protein variants from at least $10^5$ target-binding protein variants obtained during the selection in step (i) using yeast surface display comprises selecting at most the top 10% of the yeast cells that express the highest level of target-binding protein variants.

\* \* \* \* \*

SEQUENCE LISTING

```
<160> NUMBER OF SEQ ID NOS: 1

<210> SEQ ID NO 1
<211> LENGTH: 97
<212> TYPE: PRT
<213> ORGANISM: Homo Sapiens

<400> SEQUENCE: 1

Val Glu Arg Ser Ser Asp Val Pro Arg Asp Leu Glu Val Val Ala Ala
1               5                   10                  15

Thr Pro Thr Ser Leu Leu Ile Ser Trp Asp Ala Pro Ala Val Thr Val
            20                  25                  30

Arg Tyr Tyr Arg Ile Thr Tyr Gly Glu Thr Gly Gly Asn Ser Pro Val
        35                  40                  45

Gln Glu Phe Thr Val Pro Gly Ser Lys Ser Thr Ala Thr Ile Ser Gly
    50                  55                  60

Leu Lys Pro Gly Val Asp Tyr Thr Ile Thr Val Tyr Ala Val Thr Gly
65                  70                  75                  80

Arg Gly Asp Ser Pro Ala Ser Ser Lys Pro Ile Ser Ile Asn Tyr Arg
                85                  90                  95

Thr
```